US007913640B2

(12) United States Patent  (10) Patent No.: US 7,913,640 B2
MacDonald et al.  (45) Date of Patent: Mar. 29, 2011

(54) MOISTURE INDICATOR FOR HEAT AND MOISTURE EXCHANGE DEVICES

(75) Inventors: John Gavin MacDonald, Decatur, GA (US); Allison Salyer Bagwell, Alpharetta, GA (US); Molly K. Smith, Atlanta, GA (US); Jeffrey E. Fish, Winston-Salem, NC (US); Jason Lye, Atlanta, GA (US); Brian J. Cuevas, Cumming, GA (US); Michael Sleva, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 516 days.

(21) Appl. No.: 11/983,696

(22) Filed: Nov. 9, 2007

(65) Prior Publication Data

US 2009/0120432 A1  May 14, 2009

(51) Int. Cl.
*A62B 7/10* (2006.01)
(52) U.S. Cl. .................. 116/206; 116/200; 128/201.13; 128/205.23; 600/532
(58) Field of Classification Search .................. 116/206, 116/200, 264, 112; 128/201.13, 204.13, 128/205.12, 205.23, 207.14; 600/529–533, 600/537–538; 73/73
See application file for complete search history.

(56) References Cited

U.S. PATENT DOCUMENTS

| | | | |
|---|---|---|---|
| 2,249,867 A * | 7/1941 | Snelling | 73/335.08 |
| 4,090,513 A | 5/1978 | Togawa | |
| 4,717,710 A * | 1/1988 | Shimizu et al. | 503/213 |
| 4,805,608 A | 2/1989 | Eckstein et al. | |
| 4,931,051 A | 6/1990 | Castello | |
| 5,058,999 A * | 10/1991 | Davis | 349/197 |
| 5,166,075 A * | 11/1992 | Fehder | 436/133 |
| 5,194,224 A | 3/1993 | Plotz et al. | |
| 5,290,516 A | 3/1994 | Greco et al. | |
| 5,375,592 A | 12/1994 | Kirk et al. | |
| 5,389,093 A * | 2/1995 | Howell | 604/361 |
| 5,468,451 A | 11/1995 | Gedeon | |
| 5,617,849 A * | 4/1997 | Springett et al. | 128/206.24 |
| 6,126,613 A | 10/2000 | Edwards et al. | |
| 6,460,539 B1 * | 10/2002 | Japuntich et al. | 128/205.27 |

(Continued)

FOREIGN PATENT DOCUMENTS

GB  2119659  11/1983

(Continued)

OTHER PUBLICATIONS

ASTM Designation: D2244-93, "Standard Test Method for Calculation of Color Differences From Instrumentally Measured Color Coordinates," Nov. 1993, pp. 210-214.

(Continued)

*Primary Examiner* — R. A. Smith
*Assistant Examiner* — Tania C Courson
(74) *Attorney, Agent, or Firm* — James B. Robinson

(57) ABSTRACT

There is provided a moisture indicator for a heat and moisture exchange (HME) device that uses a pre-colorant and an activator applied to an inner surface of the HME device. The colorant undergoes a color change of Delta E ($\Delta E$) of equal to or greater than 3 units upon exposure to moisture but not upon exposure to high humidity. The colorant is visually obvious to the unaided human eye under normal light conditions through the body of the device. The HME device with the visual indicator for moisture can indicate to the care-giver that it is time to change the HME device.

14 Claims, 2 Drawing Sheets

U.S. PATENT DOCUMENTS

| | | | |
|---|---|---|---|
| 6,622,816 B2 * | 9/2003 | Falco et al. | 181/135 |
| 6,732,733 B1 * | 5/2004 | Brostrom et al. | 128/206.27 |
| 6,769,430 B1 | 8/2004 | Carlsen et al. | |
| 6,815,207 B2 * | 11/2004 | Yabuki et al. | 436/2 |
| 7,159,532 B2 | 1/2007 | Klofta | |
| 7,178,571 B2 | 2/2007 | Vergona | |
| 7,188,622 B2 * | 3/2007 | Martin et al. | 128/206.15 |
| 7,624,731 B2 * | 12/2009 | Walstrom | 128/201.13 |
| 7,682,696 B2 * | 3/2010 | Dean et al. | 428/412 |
| 2003/0023182 A1 * | 1/2003 | Mault et al. | 600/532 |
| 2003/0056710 A1 | 3/2003 | Radmacher et al. | |
| 2003/0105407 A1 * | 6/2003 | Pearce et al. | 600/532 |
| 2004/0255952 A1 | 12/2004 | Carlsen et al. | |
| 2007/0157702 A1 * | 7/2007 | Hamada | 73/29.04 |
| 2008/0075870 A1 * | 3/2008 | Ambrose et al. | 427/387 |
| 2008/0271739 A1 * | 11/2008 | Facer et al. | 128/206.19 |
| 2008/0289535 A1 * | 11/2008 | Spector | 106/31.13 |
| 2009/0013760 A1 * | 1/2009 | Chiba et al. | 73/29.04 |
| 2009/0205659 A1 * | 8/2009 | Belluzzi et al. | 128/204.17 |
| 2009/0223432 A1 * | 9/2009 | Kodama et al. | 116/206 |
| 2009/0255535 A1 * | 10/2009 | Kanzer | 128/206.14 |
| 2009/0270710 A1 * | 10/2009 | Copp et al. | 600/396 |
| 2009/0301474 A1 * | 12/2009 | Korneff et al. | 128/201.13 |

FOREIGN PATENT DOCUMENTS

| | | | |
|---|---|---|---|
| GB | 2306346 A | * | 5/1997 |
| JP | 63264683 A | * | 11/1988 |
| JP | 08-092511 A | | 4/1996 |

OTHER PUBLICATIONS

ASTM Designation: E308-90, "Standard Test Method for Computing the Colors of Objects by Using the CIE System", Feb. 1991, pp. 244-270.

* cited by examiner

MOISTURE INDICATOR FOR HEAT AND MOISTURE EXCHANGE DEVICES

BACKGROUND OF THE INVENTION

In intensive care therapy, ventilators (also called respirators) are used for mechanical ventilation of the lungs of a patient. The ventilator unit is connected to a hose set; the ventilation tubing or tubing circuit, delivering the ventilation gas to the patient. At the patient end, the ventilation tubing is typically connected to a tracheal ventilation catheter or tube, granting direct and secure access to the lower airways of a patient. Heat and moisture exchange (HME) devices are used as part of the breathing tube system for patients requiring breathing assistance or air supply. They are typically located at the patient end of the tubing, adjacent the tracheal catheter.

In normal, unassisted respiration, heat and moisture are absorbed from the exhaled air by the inner walls of the oral and nasal cavities and the pharynx as it travels from the lungs to the outside environment. This heat and moisture is then transferred to the inhaled air in the next breath, helping to keep the mucus membranes of the lungs humidified and at the proper temperature. Mechanical ventilation the lungs bypasses this natural system, resulting in warm, dry air being introduced to the lungs. After a period of time, the respiratory tract of a ventilated patient becomes dried, causing pain and discomfort and possibly causing lung damage.

HME devices are placed in the ventilator circuit at a point where the warm, moist air leaves the patient. The exhaled air immediately enters the device, where the moisture and heat are absorbed by materials disposed in the path of the flow of air. These layers then impart the absorbed heat and moisture to the inhaled air in the next breath. The retention of warmth and the high humidity prevent the patient's lungs and mucus layers from drying out. In addition, HME devices can act as a viral filters to prevent viruses from entering the breathing air supply of the patient.

While warmth and humidity are desired in the lungs, liquid moisture is not. Liquid moisture prevention is usually provided by specialized foam in the HME device which functions to trap any liquid moisture from entering the lungs. With time, however, moisture can build up in the foam causing an increase in the pressure drop across the device. This greater pressure drop increases the effort that must be expended by the patient and can cause the patient to labor to breathe. At present, the care giver observes the labored breathing of the patient and uses this as the signal to change out the HME device.

Rather than require each patient to fatigue himself by laboring to breathe, It would clearly be useful to have an indicator of some sort built into the device to alert the caregiver that the HME device has a certain level of moisture and needs to be changed.

SUMMARY OF THE INVENTION

Disclosed herein is a HME device with a visual indicator for moisture that can indicate to the care-giver that it is time to change the device. Furthermore, since hospital emergency wards have so many audio alarms and buzzers in use as warnings, the proposed device may have a vivid color change that can be observed from some distance. If desired, a secondary (e.g. electronic) color sensing alarm may be used with the moisture indicator to detect the color change and provide an audio or electronic signal. The color change of the indicator is triggered by liquid moisture and is not triggered by high humidity, even up to 95% levels.

DETAILED DESCRIPTION OF THE INVENTION

Heat and moisture exchange (HME) devices retain heat and moisture expelled from a patient during an exhalation and return it to the patient upon inhalation, thus helping prevent irritation due to cooling and dessication of the trachea and lungs. HME devices may be used to replace the heating and moisturizing normally provided by the nose, whenever the nose is bypassed in the breathing process, such as when a patient is placed on a ventilator or respirator, or when breathing on his own after a tracheostomy. An example of an HME device may be found in U.S. Pat. No. 4,090,513.

Figure 1:
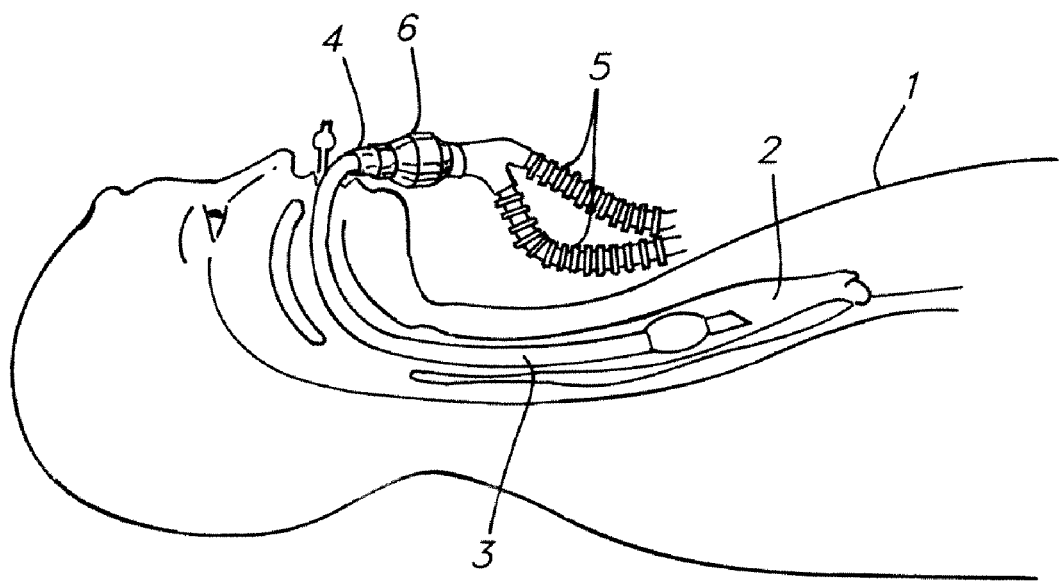
FIG. 1 is a drawing of a patient undergoing mechanical ventilation and using an HME device.

As can be seen in FIG. 1, the patient 1 has an airway 2 in which has been placed an entdotracheal tube 3. The tube has a connector 4 which allows the HME device 6 to be attached between the tube 3 and the ventilator tubing legs 5. The ventilator (not shown) supplies air to one leg of the ventilator tubing and removes air from the other leg of the ventilator tubing, thus providing adequate breathing air to the patient.

Figure 2:
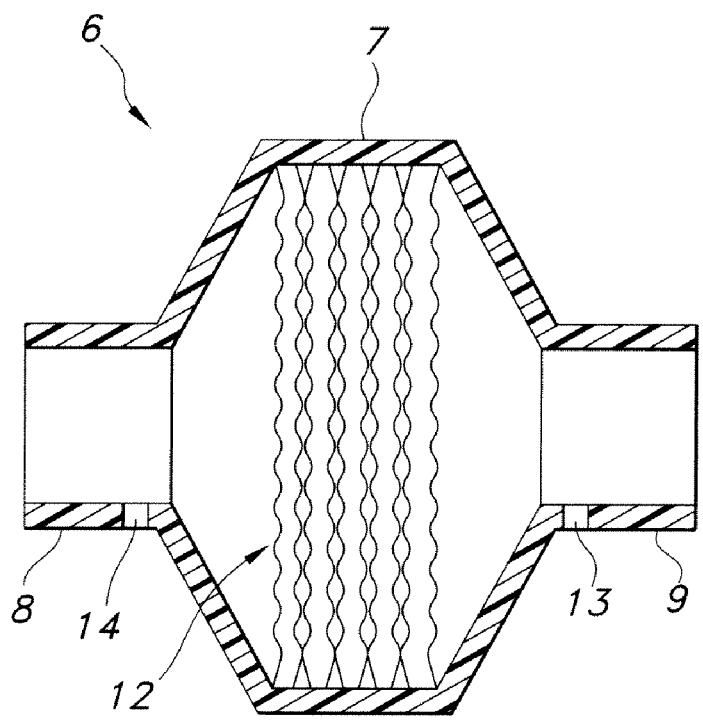
FIG. 2 is a cross-sectional drawing of an HME device.

FIG. 2 is a cross-sectional view of the HME device 6 of FIG. 1, the device 6 has an inlet 8 with a tube insertion hole 14 and an outlet 9 with a tube insertion hole 13, an enlarged central portion 7 housing the heat and moisture exchange body 12. The exchange body 12 may comprise layers perpendicular to the flow or air or may comprise, for example, porous foam, or mixtures thereof. The HME body may also be shaped in such a manner as to allow the passage of an aspirating catheter therethrough, such as is illustrated in US patent publication 2004/0255952.

In an alternative embodiment, not shown, the HME device may have only an inlet and tube insertion hole but no single outlet, instead having multiple openings on the outlet side. This embodiment may be used when ventilator assist of the patient is not necessary but warming and moisturizing of the breathing air is desired.

The problem that remains unsolved in the prior art is to know when the HME device is saturated with water and needs to be changed, without relying on the labored breathing of the patient as the signal. The HME device described herein signals when the device is saturated by changing color. The device only develops color on exposure to moisture and not when exposed to high humidity. The indicators disclosed herein feature a colorless pre-colorant which, when mixed with an activator, remains colorless when exposed to high humidity (>95% and 37° C.) for 24 hours, yet when exposed to moisture (liquid water), quickly (<1 min) develops color to generate a vivid color signal, i.e. a color change Visible to the unaided human eye under normal lighting conditions or with a Delta E equal to or greater than 3.0 units.

L*a*b* color values measurements (CIE 1976 Commission Internationale de l'Eclairage) can be used to generate a Delta E value that is indicative of the degree of color change of a sample. Delta E is calculated in accordance with the following equation:

$$\text{Delta } E = SQRT[(L^*\text{standard} - L^*\text{sample})^2 + (a^*\text{standard} - a^*\text{sample})^2 + (b^*\text{standard} - b^*\text{sample})^2]$$

The higher the Delta E, the greater the change in color intensity. Unless the color's intensity is increased by a curing step, a large increase in delta E would typically be indicative of fading. Testing may be carried out in accordance with ASTM DM 224-93 and ASTM E308-90. Where values for delta E are less than 3.0 units, it is generally accepted that such color change cannot be observed with the human eye under normal lighting conditions. A detailed description of spectrodensitometer testing is available in *Color Technology in the Textile Industry*, 2nd Edition, Published 1997 by AATCC (American Association of Textile Chemists & Colorists).

The intensity or brightness of light is expressed in lux (lx), for example, an over cast summer day is estimated to between 30,000 lx and 40,000 lx and a mid-winter day is estimated to be about 10,000 lx. The British Standards Institution Code of Practice for Day-lighting, BS 8206 Part 1 deals in general terms with the code of practice for artificial light. The following gives some general guidance for the light requirements for the work place.

General office, laboratories, kitchen—500 lx
Drawing offices—750 lx
Tool rooms and paintwork—100 lx
Inspection of graphic reproduction—1500 lx.

Accordingly, for purposes of the present invention "normal light conditions" refers to light conditions of between about 500 lx and 2000 lx, more desirably, from about 750 lx to about 1500 lx as determined in accordance with BS 8206 part 1.

Figure 3:
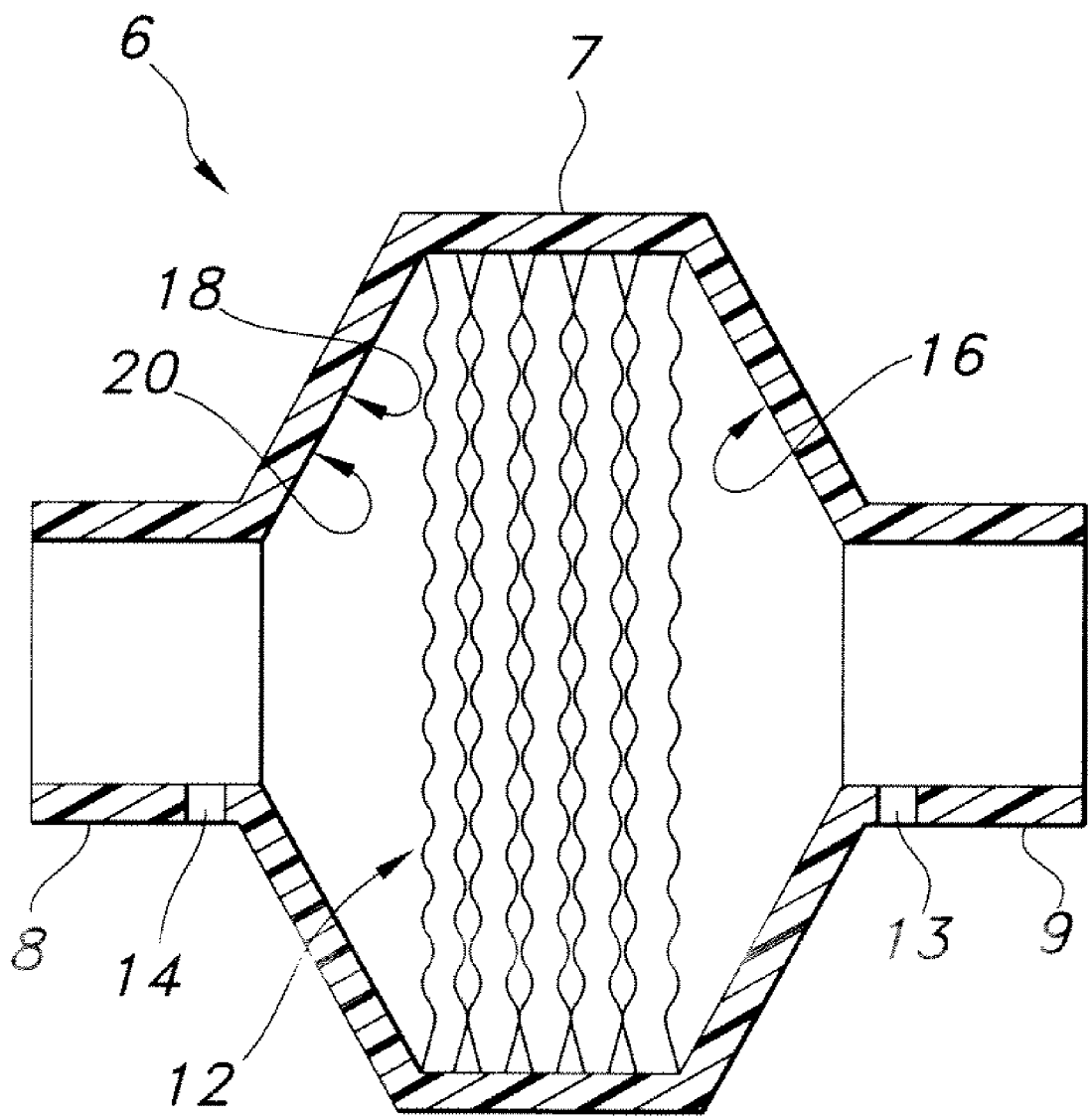
FIG. 3 is a cross-sectional drawing of an HME device including the moisture indicator disclosed herein.

The pre-colorant 18 (FIG. 3) and activator 20 (FIG. 3) may be applied to the inside of the HME so that it is exposed to the conditions inside the device. It may be applied to the inside surface 16 (FIG. 3) of the enlarged central portion 7 of the HME device, provided of course that the body of the device in that portion is transparent, or sufficiently translucent that the color change is observable by the unaided human eye through the body of the device under normal light conditions.

The pre-colorant may be a lactone such as methyl violet lactone, malachite lactone, fluorescein, phenolphthalein, thymolphthalein, leuco methylene blue for example.

The pre-colorant or mutable colorant may be a dye classified under the above list such as rose bengal, neutral red, alizarin, crystal violet, erythrosine, methyl green, methyl violet, eosin y, bromophenol blue, congo red, bromochlorophenol blue, ethyl orange, bromocresol green, cochineal, chlorophenol red, bromocresol purple, nitrazine yellow, bromothymol blue, neutral red, etc.

The activator may be an acid such as 2-sulfosalicylic acid, ascorbic acid, citric acid, malic acid, oxalic acid, lactic acid, p-toluenesulfonic acid, methane-sulfonic acid etc.

It is believed that the use of these compounds in the HME device will pose no hazard to patients breathing through it as they should remain fixed in place on the HME device and not migrate into the air stream passing through the HME device. Even if this should be incorrect, it's believed that the concentration of such compounds in the air stream would be of such a low level that no detrimental effects would be caused.

The amount of pre-colorant in the composition applied to the HME device may be an amount effective to be seen with the unaided human eye under normal lighting conditions. This amount may vary depending on the degree of transparency of the HME device. The effective amount or effective concentration of pre-colorant required would obviously be less for a device that was completely transparent. Likewise the effective amount of pre-colorant needed would be greater for a translucent device. Suitable ratios of colorant to activator are 1:100, 1:50, 1:20 and 1:10.

The compositions of the examples below were powders. They may be mixed with a fugitive solvent to apply them. Such solvents include any non-aqueous based solvent. Particularly suitable solvents are acetone, ethanol (100%), iso-propanol (100%), toluene, xylenes, acetonitrile, DMF (dimethyl formamide), DMSO (dimethyl sulphoxide), ethyl acetate, petroleum spirits (pet ether), etc.

The composition may also be incorporated into a paper-based label using the above solutions and allowed to dry. In this manner the composition may be printed onto a label using known printing methods and the label applied to the inside of the HME device. The composition may be applied onto the device in a pattern such as a stripe, dot, square, line, circle, star, flower etc. Additionally the powder composition may be dispersed into water soluble or dispersible resins or adhesives which could be printed onto the HME device itself. The composition may be applied as a powder coating, adhesive binder coating, paper coating, paper sticker or resinous coating The invention is illustrated by the following examples. While this composition may be applied by any commercially known method, it was applied in the examples using merely an artist's brush, and allowed to dry.

Example 1

Crystal violet lactone (1.0 g, from Aldrich Chemical Company, Milwaukee Wis.) was mixed with an equal amount of 2-sulfosalicylic acid (also from Aldrich) to give an off-white colored powder. This powder (0.3 g) was placed on a glass slide and spread out to give a thin coating. The slide was placed into an incubating oven (at 37° C. and >95% humidity) for 24 hours. The off-white powder did not show any signs of color development. In contrast, when 0.5 ml of water was placed on a sample of the powder mixture a blue color rapidly developed, i.e., in less than one minute.

Example 2

Malachite Green lactone (1.0 g from Aldrich) was mixed with an equal amount of 2-sulfosalicylic acid to give an off-white colored powder. This powder (0.3 g) was placed on a glass slide and spread out to give a thin coating. The slide was placed into an incubating oven (at 37° C. and >95% humidity) over night. The off-white powder did not show any signs of color development. In contrast, when 0.5 ml of water was placed on a sample of the powder mixture the green color rapidly developed in less than one minute.

Example 3

Cochineal (1.0 g, Sigma Chemical Company, St. Louis Mo.) was mixed with an equal amount of 2-sulfosalicylic acid to give a violet colored powder. This powder (0.3 g) was placed on a glass slide and spread out to give a thin coating. The slide was placed into an incubating oven (at 37° C. and >95% humidity) over night. The violet powder did not show any signs of color development. In contrast, when 0.5 ml of water was placed on a sample of the powder mixture the purple color changed to a bright red color in less than 3 minutes.

Example 4

Cochineal was mixed with an equal amount of ascorbic acid (from Aldrich) to give a violet colored powder. This powder (0.3 g) was placed on a glass slide and spread out to give a thin coating. The slide was placed into an incubating oven (at 37° C. and >95% humidity) over night. The violet powder did not show any signs of color development. In contrast, when 0.5 ml of water was placed on a sample of the powder mixture the purple color changed to a bright red color in less than 3 minutes.

Example 5

Neutral Red (1.0 g from Aldrich) was mixed with an equal amount of 2-sulfosalicylic acid to give a yellow colored powder. This powder (0.3 g) was placed on a glass slide and spread out to give a thin coating. The slide was placed into an incubating oven (at 37° C. and >95% humidity) over night. The yellow powder did not show any signs of color development. In contrast, when 0.5 ml of water was placed on a sample of the powder mixture the bright red color rapidly developed in less than one minute.

Example 6

Alizarin (0.2 g from Aldrich) was mixed with an equal amount of 2-sulfosalicylic acid to give a red colored powder. This powder (0.3 g) was placed on a glass slide and spread out to give a thin coating. The slide was placed into an incubating oven (at 37° C. and >95% humidity) over night. The red powder did not show any signs of color development. In contrast, when 0.5 ml of water was placed on a sample of the powder mixture the yellow color rapidly developed in less than one minute.

Example 7

0.5 g of the powder mixture described in example 1 was mixed into 1 g of rubber cement (Elmer's. Products Inc, Columbus Ohio) to give a white paste. 0.3 g of this paste was then spread over a microscope glass slide to yield a thin coating. The slide was placed into an incubating oven (37° C. and >95% humidity) over night. The white coating did not show any signs of color development. In contrast, when 0.5 ml of water was placed on the coated slide the white colored coating rapidly turned blue color developed in less than three minutes.

As will be appreciated by those skilled in the art, changes and variations to the invention are considered to be within the ability of those skilled in the art. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

What is claimed is:

1. A moisture indicator for a Heat and Moisture Exchange (HME) device comprising a pre-colorant and an activator, applied to an inner surface of said device, wherein said colorant changes from colorless to colored upon exposure to moisture but not upon exposure to high humidity and said change is visible through a body of said device.

2. The moisture indicator of claim 1 wherein the indicator is visually obvious to the unaided human eye under normal light conditions.

3. The moisture indicator of claim 1 wherein the indicator undergoes a color change of Delta E (ΔE) of equal to or greater than 3 units.

4. The indicator of claim 1 wherein the pre-colorant is selected from the group consisting of methyl violet lactone, malachite lactone, fluorescein, phenolphthalein, thymolphthalein, leuco methylene blue, rose bengal, neutral red, alizarin, crystal violet, erythrosine, methyl green, methyl violet, eosin y, bromophenol blue, congo red, bromochlorophenol blue, ethyl orange, bromocresol green, cochineal, chlorophenol red, bromocresol purple, nitrazine yellow, bromothymol blue, neutral red and mixtures thereof.

5. The indicator of claim 1 wherein the activator is selected from the group consisting of carboxylic acid-based or sulfonic acid-based acids.

6. The indicator of claim 1 wherein the activator is selected from the group consisting of 2-sulfosalicylic acid, ascorbic acid, citric acid, malic acid, oxalic acid, lactic acid, p-toluenesulfonic acid, methanesulfonic acid.

7. The indicator of claim 1 wherein the time taken to change color is less than one minute.

8. The indicator in claim 1 is on the device as a stripe, dot, square, pattern, line, circle, star, flower or a pattern of the same.

9. The indicator of claim 1 is applied as a powder coating, adhesive binder coating, paper coating, paper sticker, resinous coating.

10. The indicator of claim 1 wherein the ratio of colorant to activator is 1:100, 1:50, 1:20, 1:10.

11. A moisture indicator for a Heat and Moisture Exchange (HME) device comprising a colorless pre-colorant and an activator applied to an inner surface a body of said device, wherein said colorant undergoes a color change of Delta E (ΔE) of equal to or greater than 3 units upon exposure to moisture but not upon exposure to high humidity and said change is visually obvious to the unaided human eye under normal light conditions, through the body of the device.

12. A Heat and Moisture Exchange (HME) device comprising:
 a central body adapted to house a heat and moisture exchange body, the central body having an inner surface and an outer surface, at least a portion of which is translucent or transparent:
 an inlet defining a tube insertion opening;
 an outlet defining a tube insertion opening;
 a heat and moisture exchange element; and
 a moisture indicator comprising a colorless pre-colorant and an activator applied to an inner surface of the central body of said device, wherein said colorant undergoes a color change of Delta E (ΔE) of equal to or greater than 3 units upon exposure to moisture but not upon exposure to high humidity and said change is visually obvious to the unaided human eye under normal light conditions, through the central body of the device.

13. The Heat and Moisture Exchange (HME) device of claim 12, wherein the moisture indicator is applied to an inner surface of the central body as a powder coating, adhesive binder coating, paper coating, paper sticker, resinous coating.

14. The Heat and Moisture Exchange (HME) device of claim 12 wherein the moisture indicator is applied to an inner surface of the central body as a stripe, dot, square, pattern, line, circle, star, flower or a pattern of the same.

* * * * *